United States Patent [19]
Bruce et al.

[11] Patent Number: 6,090,999
[45] Date of Patent: Jul. 18, 2000

[54] PLUG FOR THE CRANIAL BONE

[75] Inventors: Ingrid Bruce; Lars Bruce, both of Viken, Sweden

[73] Assignee: Lanka Limited, Isle of Man, United Kingdom

[21] Appl. No.: 09/068,030

[22] PCT Filed: Oct. 31, 1996

[86] PCT No.: PCT/SE96/01400

§ 371 Date: Jun. 23, 1998

§ 102(e) Date: Jun. 23, 1998

[87] PCT Pub. No.: WO97/16136

PCT Pub. Date: May 9, 1997

[30]     Foreign Application Priority Data

Oct. 31, 1995  [SE]  Sweden .................................. 9503844

[51] Int. Cl.[7] .................................................. A61F 2/28
[52] U.S. Cl. ................... 623/16; 606/72; 128/887
[58] Field of Search ............................ 128/887; 433/173, 433/175; 623/16, 15; 606/72–74

[56]            References Cited

U.S. PATENT DOCUMENTS

| 3,717,932 | 2/1973 | Brainin ................................... 433/175 |
| 4,950,295 | 8/1990 | Weigum et al. .......................... 623/16 |
| 5,201,738 | 4/1993 | Scott et al. ............................... 606/72 |
| 5,263,986 | 11/1993 | Noiles et al. ............................ 623/16 |
| 5,383,932 | 1/1995 | Wilson et al. ............................ 606/95 |
| 5,427,526 | 6/1995 | Fernandes .............................. 433/175 |
| 5,545,224 | 8/1996 | Israelsen .................................. 623/15 |
| 5,569,250 | 10/1996 | Sarver et al. ............................ 606/72 |
| 5,571,017 | 11/1996 | Niznick .................................. 433/175 |
| 5,707,373 | 1/1998 | Sevrain et al. ........................... 606/72 |

FOREIGN PATENT DOCUMENTS

| 0469441 A1 | 2/1992 | European Pat. Off. . |
| 3505567 A1 | 2/1985 | Germany . |
| 682450 A5 | 9/1993 | Switzerland . |

*Primary Examiner*—Mickey Yu
*Assistant Examiner*—Bruce E Snow
*Attorney, Agent, or Firm*—Smith, Gambrell & Russell, LLP

[57]            ABSTRACT

A method for inserting a plug into a hole formed in a cranial bone by rotating the plug to insert. The plug having a body with a first end, a second end, and a peripheral surface interposed there between, the first end is slightly larger than the second end. The peripheral surface further includes irregularly distributed projections.

8 Claims, 1 Drawing Sheet

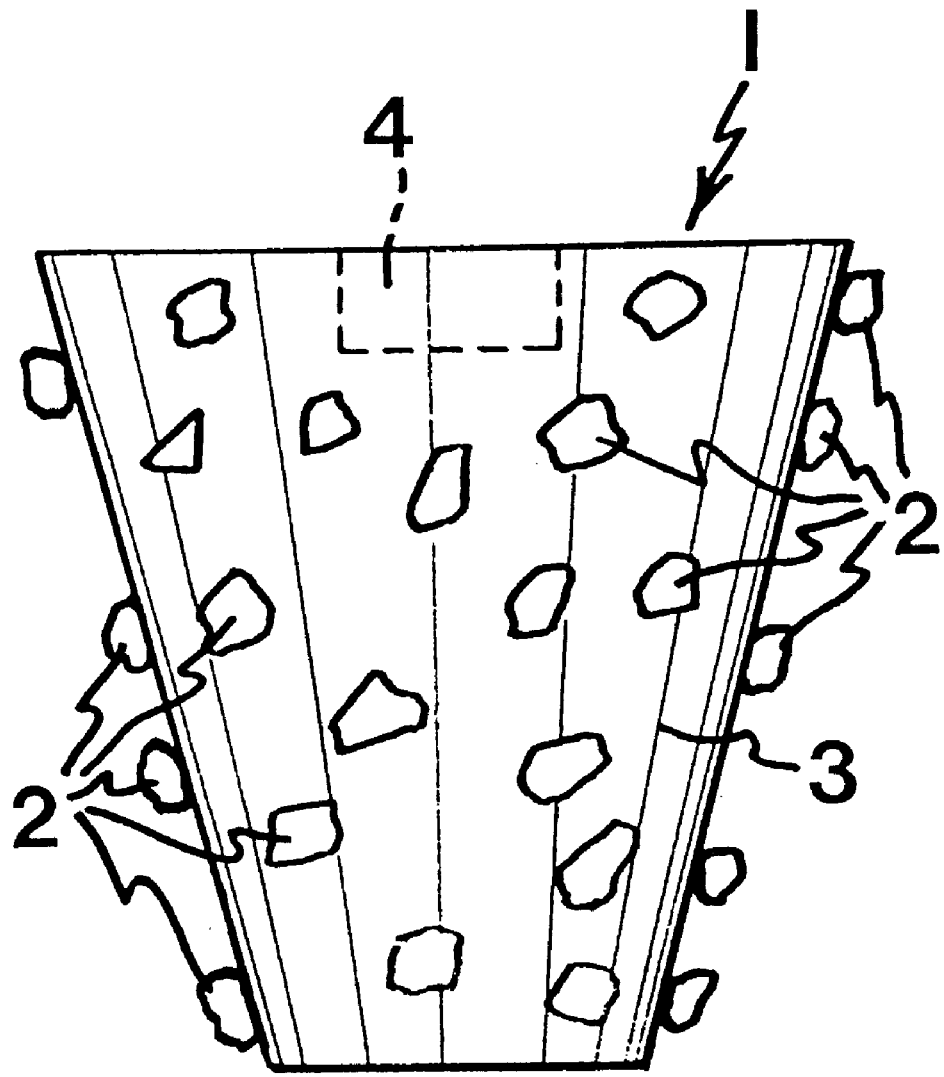

PLUG FOR THE CRANIAL BONE

The present invention relates to a plug for the cranial bone.

An operation in the head or skull, which is required, for instance, in case of brain tumour or cerebral haemorrhage, is in most cases begun with the removal of a piece of the cranial bone. To this end, a number of spaced-apart holes are drilled in the cranial bone along a contour line corresponding to the periphery of the piece of cranial bone to be removed, whereupon the cranial bone is sawn through between the drill holes such that the piece of cranial bone is released and can be removed. After performing the operation, the piece of cranial bone is restored, and straight-circular-cylindrical plugs are inserted in the drill holes. At present the plugs consist in most cases of hydroxyapatite and have a head like a fungus. Under the scalp, the head of the plug rests against the outside of the skull and prevents the plug from falling into the skull.

The projecting head of the plug causes a cosmetic problem. The circular-cylindrical shape of the plug results in a poor fit in the hole and consequently a long healing period. This is caused by the fact that it is not possible to drill in a consequently circular-cylindrical manner. The drill holes will often be elliptic or have a shape deviating from a circular cross-section. Hydroxyapatite breaks easily, for instance when subjected to a blow.

The object of the invention is to remedy the above-mentioned drawbacks.

The object is achieved by means of a plug according to the characterising clause of claim 1, according to which the plug consists of a conical body, in whose large end face a depression or depressions is/are formed for engagement of the plug by means of a plug-turning tool and whose circumferential surface is provided with irregularly distributed projections.

The inventive plug thus has no head, and its irregularly distributed projections accomplish, as the plug is turned into the skull, rasping-off of necrosis in the wall of the drill hole and levelling-out of wrong drillings and, consequently, a close engagement of at least portions of the outside of the plug with and in the wall of the hole. The plug is turned in until its large end face is aligned with the cranial bone.

It should be noted that, for instance, in tooth implantations, corrections for wrong drillings have already been made by using progressively increasing drill diameters, but such time-consuming measures cannot be taken when operating in the skull, for example after a cerebral haemorrhage.

The turning of plugs without heads in cavities in the human body is per se known, but only, as far as the applicant is aware, in connection with plugs whose body is threaded, see e.g. EP-A-469,441 and DE-A-3,505,567, and which are intended to serve as fixing screws for implants or which are straight-circular-cylindrical. Such screws do not yield the rasping effect aimed at by the invention.

The inventive plug may consist of any osseointegrating or biocompatible material whatever, of which the currently most preferred is titanium.

The manufacture of the plug according to the invention can take place, for instance, by diecasting of titanium.

It is understood that the transverse dimension of the plug should be adapted to the transverse dimension of the drilled hole so as to bring about the above-described rasping effect, the surgeon being supplied with plugs having different basic dimensions.

The projections have a length starting from the body and radially outwards, and a width transversely of said direction, of 1.5 mm at most, since greater lengths and widths may create problems of bone growing into the body of the plug and with the turning-in of the plug.

For optimum tissue ingrowth against the body of the plug, the projections should be undercut, i.e. have a relatively narrow base adjacent to the body. They may be, for example, grain- or ball-shaped.

An embodiment of the invention is illustrated in the accompanying drawing in longitudinal section.

A straight-conical, symmetrical plug 1 of titanium, without head, for insertion into the skull after an operation has the following dimensions: large diameter 7 mm, small diameter 6 mm and height 4 mm, the diameter figures including 0.6 mm ø ball-shaped projections 2 formed on a body 3, said projections being irregularly distributed on the circumferential surface of the body. The large end face of the plug is formed with a square depression 4 for engagement of the plug for rotation by means of a square spanner.

We claim:

1. A method for inserting a plug into a cranial bone comprising placing a plug for the cranial bone into a hole in the cranial bone and rotating the plug to insert and secure the plug, said plug comprising a body with a first end, a second end, and a peripheral surface interposed there between wherein the first end is at least slightly larger than the second end and wherein the peripheral surface further comprises irregularly distributed projections.

2. The method according to claim 1 wherein said plug is a truncated substantially conical shaped member and wherein the peripheral surface is a circumferential surface.

3. The method according to claim 1 wherein said first end of said plug further comprises a end face with one or more depressions.

4. The method according to claim 3 wherein the depression is adapted for engagement by a plug-turning tool.

5. The method according to claim 1 wherein at least some of the projections are undercut projections.

6. The method according to claim 5 wherein at least some of the projections are grain-shaped or ball-shaped.

7. The method according to claim 1 wherein the projections are 1.5 mm or less in length.

8. The method according to claim 1 wherein the plug is at least in part made of titanium.

* * * * *